United States Patent [19]

Parks

[11] Patent Number: 5,540,916
[45] Date of Patent: Jul. 30, 1996

[54] ODOR SORBING PACKAGING

[75] Inventor: Christopher J. Parks, Ellicott City, Md.

[73] Assignee: Westvaco Corporation, New York, N.Y.

[21] Appl. No.: 433,167

[22] Filed: May 3, 1995

Related U.S. Application Data

[62] Division of Ser. No. 166,823, Dec. 15, 1993.

[51] Int. Cl.[6] .................................. A61L 9/00; A61L 9/01
[52] U.S. Cl. ........................................ 424/76.1; 424/400
[58] Field of Search ........................ 424/76.1; 428/34.2; 162/138

[56] References Cited

U.S. PATENT DOCUMENTS

| | | | |
|---|---|---|---|
| 2,593,146 | 4/1952 | Howard | 154/50 |
| 3,149,023 | 9/1964 | Bodendorf et al. | 162/135 |
| 4,160,503 | 7/1979 | Ohlbach | 206/328 |
| 4,504,290 | 3/1985 | Pontius | 96/153 |
| 4,517,308 | 5/1985 | Ehlenz | 502/401 |
| 4,711,702 | 12/1987 | Hood | 162/123 |
| 4,889,750 | 12/1989 | Wiley | 428/34.2 |
| 5,122,399 | 6/1992 | Farrell et al. | 428/34.2 |
| 5,153,061 | 10/1992 | Cavagna et al. | 428/325 |

*Primary Examiner*—Thurman K. Page
*Assistant Examiner*—W. Benston

[57] ABSTRACT

Paperboard packaging material is disclosed for use in the manufacture of cartons for products which give off significant odors or aromas. The packaging material is treated to absorb odors generated by the products packaged in the packaging material. For this purpose, the paperboard packaging material is coated on one surface with an odor sorbing coating composition comprising activated carbon dispersed in an aqueous binder system. The odor sorbing coating covers substantially all interior surfaces of cartons formed from the packaging material to provide an effective concentration of activated carbon sufficient to render the contents substantially odor-free.

2 Claims, 1 Drawing Sheet

ODOR SORBING PACKAGING

BACKGROUND OF THE INVENTION

This is a divisional of copending U.S. application Ser. No. 08/166,823, filed Dec. 15, 1993.

The present invention relates generally to packaging, and more particularly to packaging which has been treated to absorb odors generated by products contained in the packaging. The packaging of the present invention is intended for products such as plastic bags or the like, but could be used for other products which generate objectionable odors or aromas.

An example of such a product is plastic food storage bags. Plastic food storage bags are manufactured from a web of material such as polyethylene by cutting blanks from the web, folding the blanks and sealing the sides of the blanks to form bags. During the edge sealing process, the conditions are ripe for producing oxidation of the polyethylene. The bags are then packaged in paperboard cartons for sale to consumers. Upon opening a carton of food storage bags, the consumer is confronted with the odor of polyethylene and oxidized polyethylene. When food is stored in such bags, these odors are often transferred to the food resulting in objectionable off-tastes. It is therefore, an object of the present invention to provide a means for absorbing such odors.

One of the most widely accepted materials used to absorb odors or the like is activated carbon. Activated carbon is used in filters, gas masks and other devices to absorb and trap objectionable odors, aromas and other impurities. One of the most common filter media forms employed for odor absorption includes a bed of activated carbon particles as taught in U.S. Pat. No. 4,504,290. Activated carbon has also found use in the manufacture of wrapping materials for products which give off objectionable odors. For example, U.S. Pat. No. 2,593,146 discloses laminated paper sheets for packaging foodstuffs wherein one of the paper sheets includes finely divided activated carbon particles uniformly distributed throughout its structure where it may act to absorb odors given off by the packaged products. In like manner U.S. Pat. No. 3,149,023 discloses another paper product which includes substantial quantities of activated carbon firmly retained therein, wherein the absorbent properties of the carbon are allegedly retained during manufacture. Meanwhile, in U.S. Pat. No. 4,517,308, a process is disclosed for making a sorptive body for the elimination of odors wherein powdered activated carbon is incorporated into a carrier strip which is used in kitchen extractor-hoods, air conditioning ducts or the like. And, finally, a coating containing activated carbon is disclosed in U.S. Pat. No. 5,153,061 (assigned to the present assignee herein), not for odor absorption, but for application to paperboard to absorb contaminants that might migrate from the paperboard at the high temperatures reached during microwave cooking. However, in each of the prior art teachings, the activated carbon applications have been made in such a way that they were either difficult to work with (e.g., the incorporation of the activated carbon in a pulp slurry), or they tended to mask the odor adsorbing capability of the activated carbon. Accordingly, it is an object of the present invention to incorporate activated carbon into a package structure in an expeditious, economical and effective manner so as to enhance and improve its adsorption powers.

SUMMARY OF INVENTION

The present invention relates generally to packaging, and more specifically to packages which have been treated to absorb the odors and aromas given off by products contained therein. For this purpose, the present invention employs activated carbon, a material well known for its ability to absorb objectionable odors, which is applied to the inside surfaces of paperboard carton blanks using conventional technology.

Activated carbon materials such as the NUCHAR products manufactured by Westvaco Corporation (the assignee herein), are available in particle sizes or can be ground to particle sizes which are readily dispersed in coatings that can be successfully applied to paperboard or the like. In particular, such material may be incorporated into ink compositions that can be printed on paper, paperboard and the like materials, suitable for making packages including cartons and containers.

It is, therefore, an object of the present invention to provide an improved method for applying an odor sorbing coating to packaging material.

It is another object of the invention to provide packages with an odor absorbing material that will accomplish the purpose of de-odorizing substantially the entirety of the package contents.

Finally, it is an object of the present invention to provide odor absorbing material on substantially all major interior surfaces of a paperboard carton to effectively de-odorize the contents of the carton.

To satisfy these and other objects the present invention contemplates the use of an activated carbon material combined with a binder that can be applied to the paperboard blanks used to make cartons, containers or the like. Solvent-based, water-based, or 100% solids binders are all possibilities for use in the present invention. In the case of solvent based binders such as ethylcellulose, nitrocellulose, polyesters, alkyds, silicones or the like, there will be a possibility of contaminating the carbon with the organic solvent. If so, the carbon would have to be reactivated after application to the substrate. In the case of 100% solids coatings, such as electron beam cured coatings, it is possible that the low molecular weight compounds used as starting materials for the electron beam coatings may also contaminate the carbon. Furthermore, the use of electron beam cured coatings requires the use of specialized curing equipment. Accordingly, water-based coatings or inks are preferred for the present invention since the binders used in such coatings present little if any interference with the capacity of the activated carbon to absorb odors. Possible water-based materials for use in the invention include acrylics, polyesters, silicones, polyvinyl acetate, polyvinyl alcohol, starch, styrene-butadiene and sodium silicate.

The preferred method for applying the odor sorbing activated carbon coatings of the present invention to the packaging substrates is by printing although coating methods such as air knife, wire wound rod or blade coaters may be employed. The rotogravure printing process may be particularly convenient where paperboard is used as the packaging material. In such a case, the same press can be used to print both the package graphics on the clay coated exterior surface of the paperboard substrate, and the odor sorbing coating in the form of an activated carbon ink composition on the uncoated interior surface of the substrate. Another advantage of using a printing process for the present invention is that with the use of pattern printing, areas of the package that require the application of adhesive for sealing the package can be kept free of the odor sorbing ink composition which might otherwise interfere with the sealing operations. In addition, printing processes allow the application of odor sorbing ink compositions in any desired amount merely by multiple overprints of the areas where the odor sorbing material is to be applied using several printing stations.

Within the odor sorbing ink composition or coating, the ratio of activated carbon to binder should be such that the maximum amount of carbon is available for odor absorption. At the same time, there should be enough binder material in the ink composition so that the carbon will not be easily abraded from the surface. If abrasion is a problem, it may be desirable to overcoat the odor sorbing ink composition or coating with a top coat which does not inhibit the effectiveness of the odor sorbing coating to adsorb odors.

DETAILED DESCRIPTION

Figure 1:
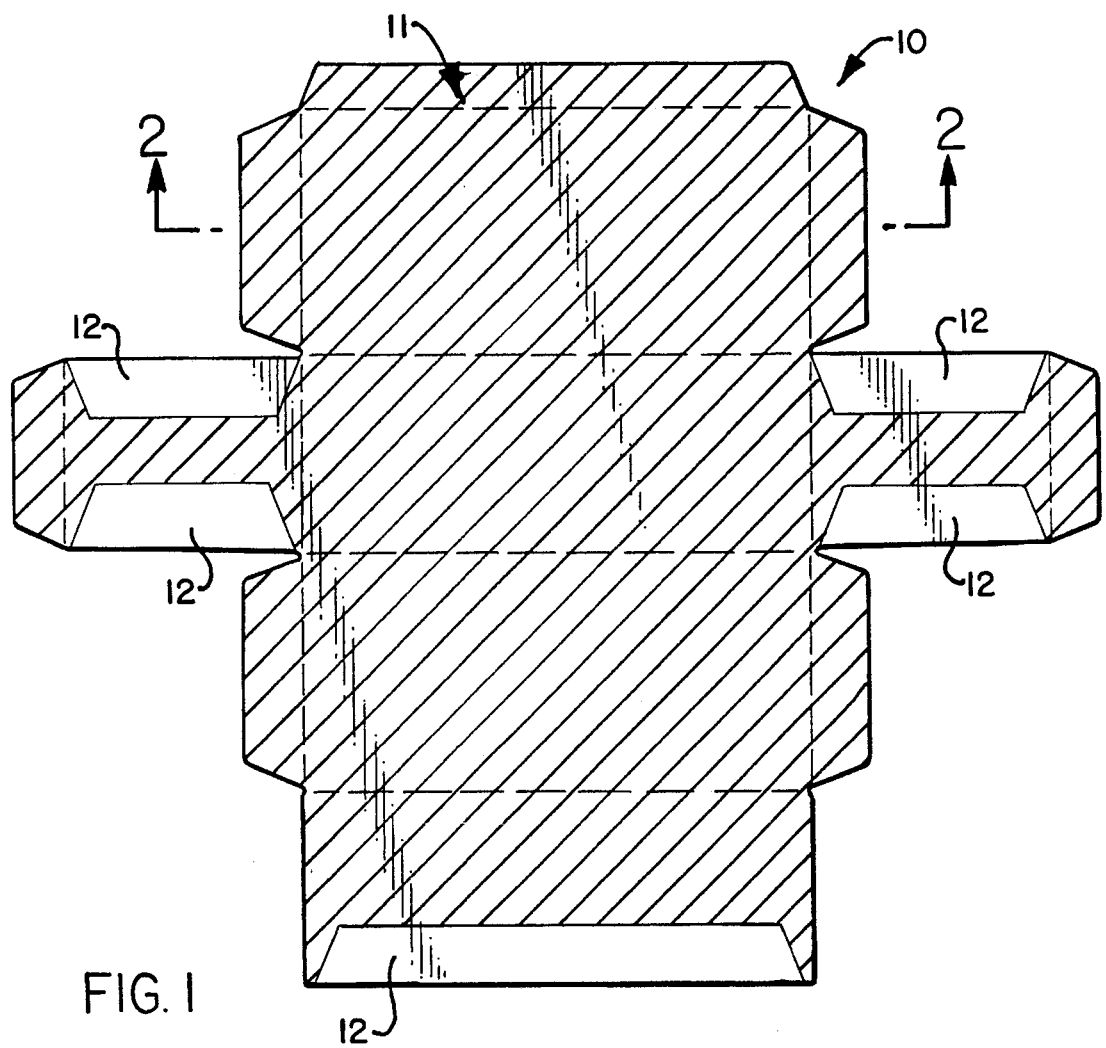
FIG. 1 is a plan view of the inside surface of a typical carton blank for a package according to the present invention which has been selectively printed with an odor sorbing ink composition; and, FIG. 2 is a cross sectional view of the blank of FIG. 1 taken along the lines 2—2.

The present invention is directed to the use of activated carbon in the manufacture of odor absorbing packaging material. In the preferred embodiment, the packaging material is prepared using a printing process. For this purpose, activated carbon is dispersed in an ink vehicle to produce an odor sorbing ink composition which may be printed on packaging material such as paperboard using conventional printing technology.

In an effort to assess the merits of the present invention, seven different water based binder systems, were chosen for evaluation using Westvaco's NUCHAR SA activated carbon. The purpose of the evaluation was to see if odor sorbing coatings could be prepared for application to paperboard. Initially it was discovered that activated carbon was not easily dispersed in either polyvinyl acetate, styrene-butadiene or acrylic binder systems. It was speculated that the activated carbon absorbed the surfactants from these binder systems. On the other hand, the activated carbon was readily dispersed in starch, polyvinyl alcohol, polyester and sodium silicate binder systems. However, since both the starch and polyvinyl alcohol binders were found to require a cooking step, development work was concentrated on the use of the polyester and sodium silicate binder systems. In order to determine the effectiveness of such coatings, a number of coating formulations were prepared using sodium silicate and polyester as the binder systems.

EXAMPLE 1

A mixture of 100 grams sodium silicate at 38.3% solids and 9.6 grams of activated carbon were dispersed in 10 grams of water. Upon thorough mixing, a coating formulation having about 40% solids was achieved with the solids content consisting of about 20% carbon and 80% binder. The carbon concentration of the coating was about 8%. Drawdowns of this coating were applied to the uncoated side of PRINTKOTE bleached paperboard (a product of Westvaco Corporation), using a No. 12 wire wound rod at a coat weight of about 26 lbs/ream (ream size 3000 ft$^2$), to a nominal thickness of about 1.2 mils. The weight of carbon in the applied coating was about 2.2 mg/in$^2$.

EXAMPLE 2

A mixture of 100 grams sodium silicate at 38.3% solids and 19.2 grams of activated carbon were dispersed in 20 grams of water. A final coating formulation having a solids of about 41% was obtained with the solids content consisting of about 33% carbon and 67% binder. The carbon concentration of the coating was about 14%. This formulation was applied to the uncoated side of paperboard samples as described in Example 1 at a coat weight of about 26 lbs/rear to a nominal thickness of about 1.2 mils. The weight of carbon in the applied coating was about 3.8 mg/in$^2$.

EXAMPLE 3

A mixture of 86.7 grams polyester at 28% solids an 12 grams of activated carbon were dispersed in 10 grams of water. This mixture produced a coating formulation having about 33% solids with the solids content consisting of about 33% carbon and 67% binder. The carbon concentration in the coating was about 11%. Drawdowns of this coating formulation were applied to the uncoated side of PRINTKOTE bleached paperboard samples as described in Examples 1 and 2 at a coat weight of about 20 lbs/ream, to a nominal thickness of about 1.2 mils. The weight of carbon in the applied coating was about 2.2 mg/in$^2$.

Samples of the coated paperboard (1 inch by 4 inch) from Examples 1, 2 and 3 were placed in 250 mil. high density polyethylene (HDPE) jars each containing a one gallon food storage bag and sealed with a screw cap. A jar with a bag and no coated paperboard sample, and an empty jar were also prepared. After 24 hours, the jars were tested by opening the screw caps and sniffing the contents. The empty jar had no discernable odor. Meanwhile, the jar containing a food storage bag and no coated paperboard sample had a distinct odor. However, the jars containing the food storage bags and the coated paperboard samples from Examples 1, 2 and 3 had reduced odor, with Example 2 being judged best followed by Example 3, and Example 1. This test demonstrated that the odor sorbing coatings were effective to reduce odor, and that the odor sorbing effect was directly related to the concentration of carbon in the applied coatings. Further development work showed that a similar odor absorbing effect could be achieved with odor sorbing coatings prepared using either starch or polyvinyl alcohol as the binder system. Coating formulations useful for the present invention preferably have a solids content of from about 30–45% depending upon the method of application. Coat weights may range from about 3–26 lbs/ream (ream size 3000 ft$^2$), and the activated carbon content of the coating may range from about 20–95%, depending upon the degree of odor absorption desired.

Accordingly it will be seen that the novelty of the present invention lies in the combination of the use of odor sorbing coatings containing activated carbon applied to the inner surfaces of paperboard cartons. The odor sorbing capacity is directly related to the concentration of carbon in the applied coating. Therefore, the amount of carbon necessary for any given application will depend upon the strength of the odor desired to be eliminated or absorbed. For the purposes of the present invention, an effective application of activated carbon is intended to mean sufficient carbon to absorb substantially all of the odor generated by a packaged product. Since the total amount of carbon required for any specific application cannot be defined with any specificity, a trial and error process may be involved. However, based on the tests conducted in Examples 1–3, it is believed that an effective carbon concentration will lie within the range of about 1–10 mg of carbon per cubic inch of the carton interior volume.

FIG. 1 of the drawing illustrates a typical paperboard blank 10 suitable for making cartons characterized by the present invention. The surface of the blank 10 is partially shaded at 11 to show the area where the odor sorbing activated carbon coating is applied. Substantially the entire surface has been shaded to demonstrate that in order to achieve the best results, substantially all interior surfaces are preferably coated with the odor sorbing coating leaving only the unshaded areas 12 for glue application. It is contemplated that for some applications, the interior surfaces of only certain major panels of the carton blank may need to be coated with odor sorbing material to achieve the desired degree of odor absorption, or the panels may only need to be coated in patterns leaving parts of each panel uncoated.

Figure 2:
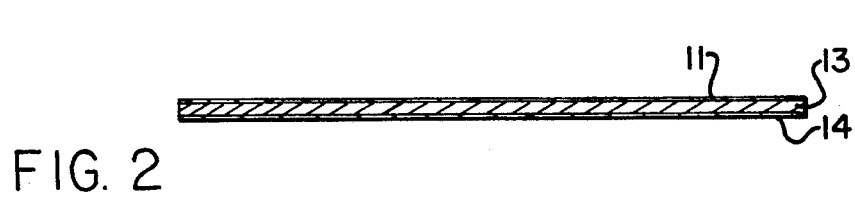

In FIG. 2, the blank 10 is typically constructed from paperboard 13 with an outer clay coated surface 14 suitable for printing graphics, and an inner activated carbon coated surface 11. The order in which the graphics and odor sorbing coating maybe applied to the paperboard is not important, except that when the graphics are applied after the odor sorbing coating, solvents and other materials used in the inks to print the graphics may be absorbed by the activated carbon layer thereby reducing its effectiveness to absorb odors from the packaged products. This can be offset to some extent with the use of low volatility water based inks for the graphics printing step, or by increasing the amount of activated carbon applied to the paperboard in the carbon application step to compensate for any loss of effectiveness.

It will thus be seen that the present invention is useful for packaging products which have objectionable odors or aromas. The invention is particularly useful for packaging such products which might come into contact with food to prevent the odors or aromas from causing off-tastes to the food. Finally the invention would be useful for packaging products which might otherwise pick up odors or off-tastes from the surrounding atmosphere including other components of the package. Thus while only preferred embodiments of the present invention have been fully shown and described, it will be obvious to those skilled in the art that various modifications and substitutions could be made in the invention without departing from the spirit and scope of the appended claims.

What is claimed:

1. An odor sorbing coating composition adapted to be applied to one surface of a paperboard substrate comprising, a mixture of activated carbon in an aqueous binder system, said coating having a solids content in the range of from about 30–45%, said solids comprising from about 20–95% activated carbon and from 5–80% binder, at a coat weight of from about 3 to 26 lbs/ream (ream size 3000 ft$^2$).

2. The odor sorbing coating composition of claim 1 wherein the binder system is selected from the group consisting of sodium silicate, polyester, starch and polyvinyl alcohol.

* * * * *